United States Patent [19]
Weaver et al.

[11] Patent Number: 5,218,973
[45] Date of Patent: Jun. 15, 1993

[54] DISPOSABLE WOUND TREATMENT ELECTRODE

[75] Inventors: Benson C. Weaver; Robert K. Mitchiner, both of Longmont, Colo.

[73] Assignee: Staodyn, Inc., Longmont, Colo.

[21] Appl. No.: 673,941

[22] Filed: Mar. 22, 1991

[51] Int. Cl.$^5$ .............................................. A61N 1/04
[52] U.S. Cl. .................................. 128/798; 128/802; 128/803
[58] Field of Search ............... 128/798, 802, 803, 640; 602/42

[56] References Cited

U.S. PATENT DOCUMENTS

| | | |
|---|---|---|
| 2,943,628 | 7/1960 | Howell . |
| 3,565,059 | 7/1971 | Hauger . |
| 4,142,521 | 3/1979 | Konikoff . |
| 4,166,457 | 9/1979 | Jacobsen et al. ............... 128/803 X |
| 4,237,886 | 12/1980 | Sakurada et al. . |
| 4,243,051 | 1/1981 | Wittemann . |
| 4,243,052 | 1/1981 | Bailey . |
| 4,248,247 | 2/1981 | Ware et al. . |
| 4,265,253 | 5/1981 | Abraham . |
| 4,300,575 | 11/1981 | Wilson . |
| 4,422,461 | 12/1983 | Glumac . |
| 4,458,696 | 7/1984 | Larimore ........................ 128/798 |
| 4,633,879 | 1/1987 | Ong . |
| 4,635,642 | 1/1987 | Cartmell et al. . |
| 4,638,796 | 1/1987 | Sims . |
| 4,640,289 | 2/1987 | Craighead . |
| 4,657,023 | 4/1987 | Kuhn . |
| 4,706,680 | 11/1987 | Keusch et al. . |
| 4,715,382 | 12/1987 | Strand . |
| 4,736,752 | 4/1988 | Munck et al. . |
| 4,738,250 | 4/1988 | Fulkerson et al. . |
| 4,771,783 | 9/1988 | Roberts . |
| 4,777,954 | 10/1988 | Keusch et al. . |
| 4,798,208 | 1/1989 | Faasse, Jr. . |
| 4,809,699 | 3/1989 | Shimizu et al. ...................... 128/640 |
| 4,817,594 | 4/1989 | Juhasz . |
| 4,846,181 | 7/1989 | Miller . |
| 4,852,571 | 8/1989 | Gadsby et al. ........................ 128/640 |
| 4,870,969 | 10/1989 | Swartz . |
| 4,893,626 | 1/1990 | Henley et al. . |
| 4,895,153 | 1/1990 | Takeuchi et al. . |
| 4,895,154 | 1/1990 | Bartelt et al. . |
| 4,895,169 | 1/1990 | Heath . |
| 4,911,657 | 3/1990 | Berlin . |
| 4,919,138 | 4/1990 | Nordenstroom . |
| 4,919,148 | 4/1990 | Muccio . |
| 4,922,906 | 5/1990 | Takeuchi et al. . |
| 4,926,878 | 5/1990 | Snedeker . |
| 4,934,383 | 6/1990 | Glumac . |
| 4,955,381 | 9/1990 | Way et al. . |
| 4,989,607 | 2/1991 | Keusch et al. .................. 128/798 X |
| 5,078,139 | 1/1992 | Strand et al. ........................ 128/640 |

FOREIGN PATENT DOCUMENTS

| | | | |
|---|---|---|---|
| 1115351 | 12/1981 | Canada ................................. | 128/798 |
| 0097436 | 1/1984 | European Pat. Off. . | |

*Primary Examiner*—Lee S. Cohen
*Attorney, Agent, or Firm*—Robert E. Harris

[57] ABSTRACT

A disposable wound treatment electrode is disclosed that is usable in combination with a releasable connector for enabling effective delivery of an electrical signal to a patient. The electrode and connector are configured so that the connector provides a readily accessible tool to facilitate disposal of the electrode after use, and a method of utilization for effecting this end is also disclosed. The electrode includes an electrically non-conductive cover sheet, an electrically conductive and preferably non-metallic disperser formed at least in part by carbon and having a portion, preferably integral with the remainder of the disperser, that extends through an aperture in the interior portion of the cover sheet, and a non-adhering wound contact sheet. In addition, protectors are provided for an integral portion of the disperser extending through the cover sheet, a retainer is provided to receive an electrically conductive skin moisturizer, and/or the peripheries of the cover sheet and the wound contact sheet are sealed together to form a closed envelope.

20 Claims, 3 Drawing Sheets

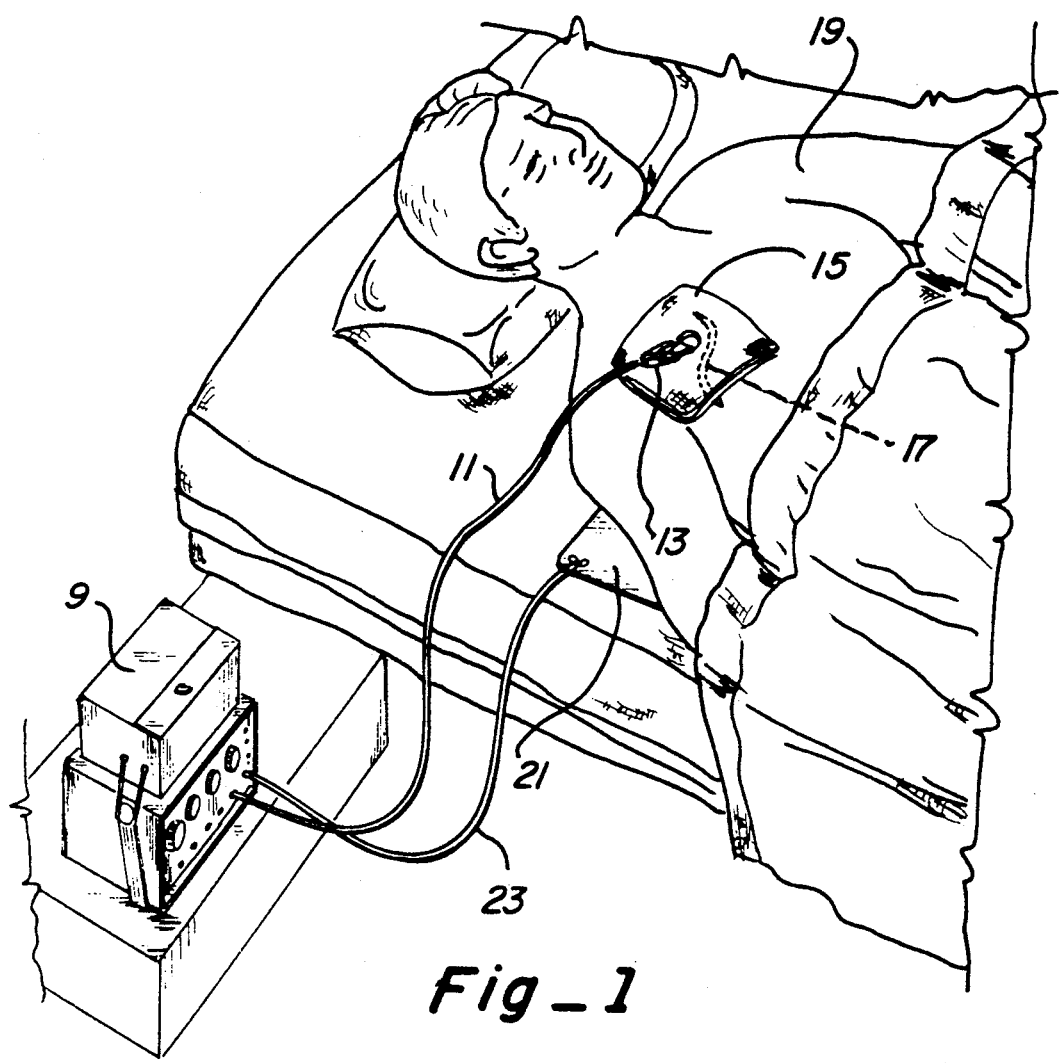
Fig_1
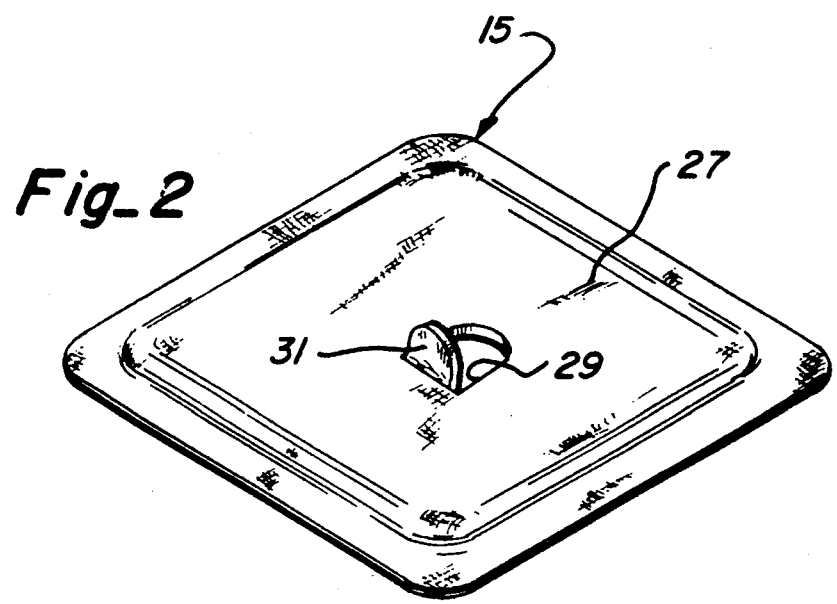
Fig_2

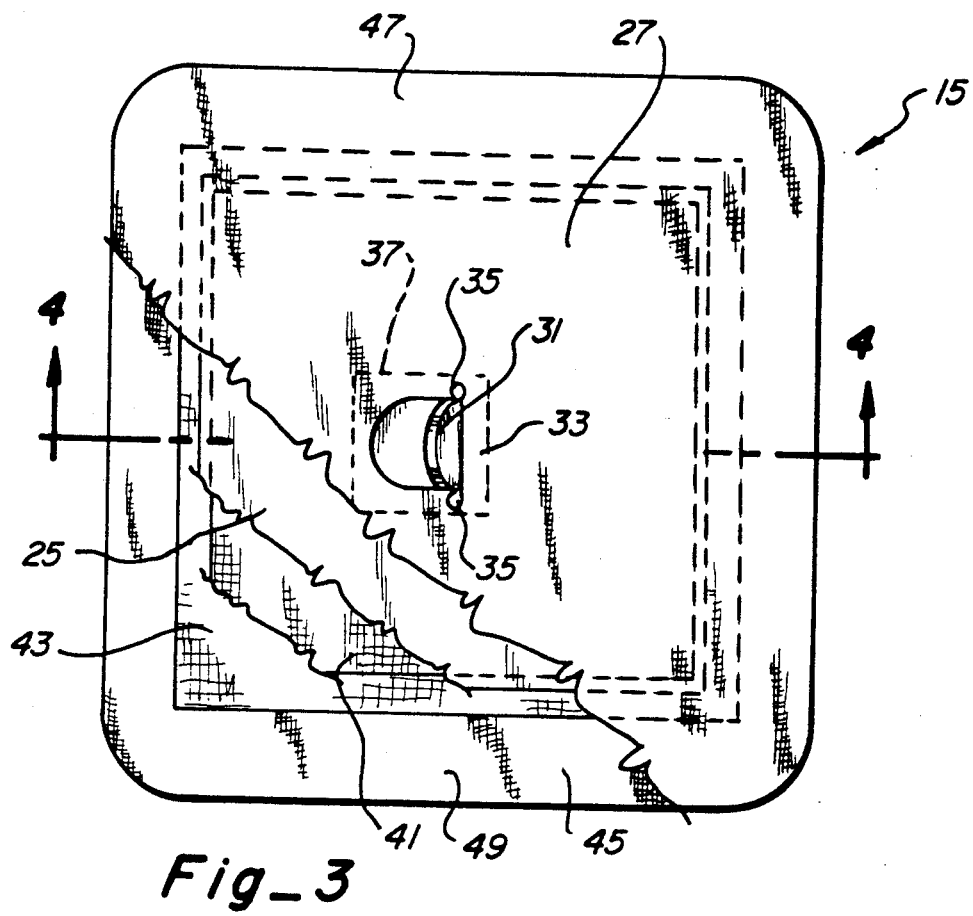
Fig_3
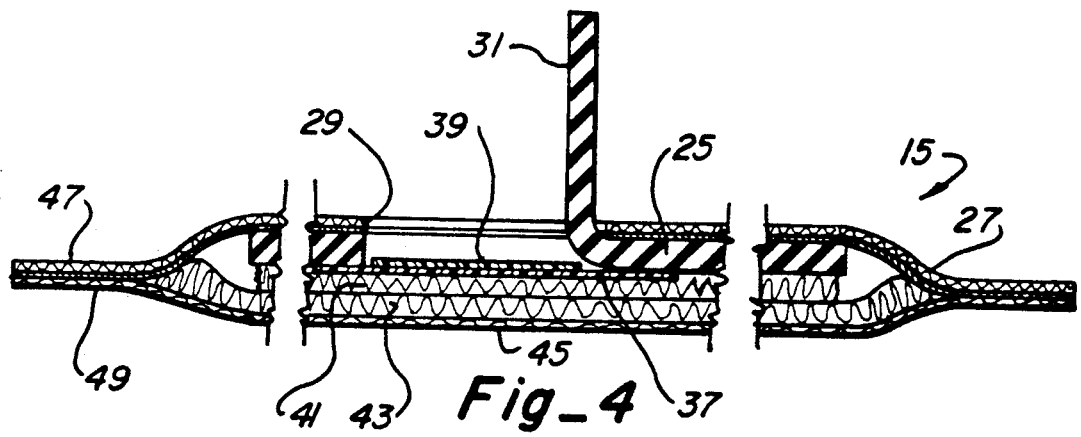
Fig_4
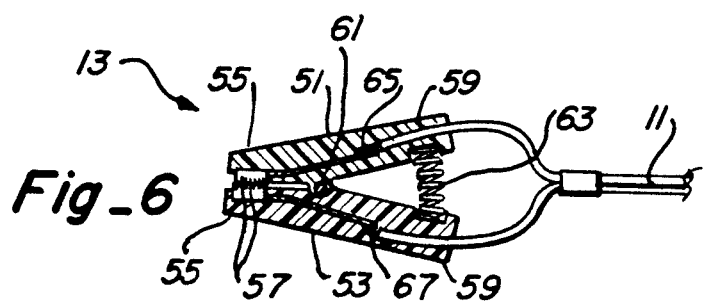
Fig_6

5,218,973

DISPOSABLE WOUND TREATMENT ELECTRODE

FIELD OF THE INVENTION

This invention relates to wound treatment, and, more particularly, relates to a disposable wound treatment electrode, combination and method for utilization.

BACKGROUND OF THE INVENTION

Skin-contacting (non-invasive) electrodes are now widely used in conjunction with medical apparatus both to monitor patient conditions and to deliver an electrical signal through the electrode to the patient, including delivery of such signals for a variety of purposes, including wound treatment, and, particularly, to enhance soft tissue wound healing.

Where the electrode is to be used in a passive manner to sense a patient condition or provide an electrical signal return path, the requirements for such an electrode are not as strenuous as are the requirements for an active electrode used to deliver a voltage or current through the skin to the patient. In like manner, the requirements for a non-invasive electrode to be in contact with intact skin is not as strenuous as are the requirements for such an electrode that is to be utilized in contact with a soft tissue wound, and particularly a soft tissue wound that is open as is most often the case.

Where the electrode is to be in contact with the wound, the electrode needs to be rated for blood contact (which requires a higher degree of biocompatibility than does an electrode that contacts intact skin), and the materials used in the electrode need to tolerate sterilization (including ability of the materials utilized to avoid break-down or thereafter present an undesirable appearance), must not be subject to ion or chemical migration (which can occur, for example, where the electrode is metallic and/or where potentially toxic materials are utilized), must not shed particles (which can occur, for example, where the skin contact layer is of cotton), and must not unduly cause corrosion (which can occur if a liquid, such as saline solution, escaping from the electrode comes into contact with metallic portions of the releasable connector through which current is applied to the electrode).

In addition, an electrode used for wound contact needs to include materials that allow contouring of the electrode to effect good wound contact over the entire area of the electrode, not include materials that prevent uniform transfer of the signal (such as current) to the patient over the entire dispersing area of the electrode, not include materials that prevent or fail to provide proper skin moisture at the wound to be healed, and be sufficiently economical to allow the electrode to be disposable from a practical standpoint.

Thus, realization of a practical and yet effective disposable wound treatment electrode to be in wound contact is not simple, and presents considerably more difficulty than would be encountered in making a passive electrode or in making an active electrode to be in contact with intact skin.

With respect to known prior art, U.S. Pat. No. 4,817,594 (Juhasz) shows a wound dressing with an envelope formed from sheets of permeable and semi-permeable material at one side and a non-adherent, wound contactable sheet of permeable material at the other side, with an electrically non-conductive charcoal fabric (chosen specifically for its anti-bacterial characteristics) engaging an electrically conductive open mesh (which may be nylon impregnated with a metal such as silver) within the envelope. Mention is also made in U.S. Pat. No. 4,817,594 that means may be provided to provide a voltage to the silver impregnated open mesh material and that good conductivity can be ensured by hydrating the dressing prior to use with isotonic saline.

U.S. Pat. No. 4,638,796 (Sims) shows a method of dressing a wound that includes use of a non-adhering barrier material, and U.S. Pat. No. 4,142,521 (Konikoff) shows electrostatic soft tissue wound repair enhancement using electret elements with gauze between the electret elements and the wound site.

U.S. Pat. No. 4,919,148 (Muccio) shows transcutaneous electrical stimulation using an electrode assembly having a carbon-rubber electrode with a boss having a bore therein to receive a connector pin, with the electrode having a non-conductive sheet at one side and a woven fabric at the other side forming an enclosure with the electrode and a gel-receiving cavity therein.

U.S. Pat. No. 4,926,878 (Snedeker) shows a medical electrode suitable for use with a TENS unit with the electrode including a stud fastener engaging a disperser layer and with the electrode having a gel, such as hydrogel, engaging the dispersive layer, while U.S. Pat. No. 4,248,247 (Ware et al.) shows a post-operative electrode with a conductive sheet formed of rubber with carbon therein, and U.S. Pat. No. 4,300,575 (Wilson) shows an air-permeable disposable TENS electrode that includes a carbon filled silicone rubber pad.

U.S. Pat. Nos. 4,934,383 and 4,422,461 (Glumac) show a TENS and/or post-operative (post-op) electrode having a metal layer and a carbon-containing conductive layer, U.S. Pat. No. 4,870,969 (Swartz) shows a medical electrode having a metal foil between a conductive plastic film and a layer of hydrogel and with a stud fastener extending through a backing layer, U.S. Pat. Nos. 4,777,954 and 4,706,680 (Keusch et al.) show an electrode with a hydrogel layer in contact with a metal snap extending through a backing, U.S. Pat. No. 4,640,289 (Craighead) shows a biomedical electrode having a metalized layer contacting a snap extending through a retainer sheet, and U.S. Pat. No. 4,633,879 (Ong) shows an electrode having a metal snap that extends through a backing to a layer of conductive adhesive.

U.S. Pat. No. 4,955,381 (Way et al.) shows a stimulating and monitoring electrode having a metal disperser with wires connected thereto extending from the electrode through a plastic foam cover and with a conductive polymer (hydrogel) layer adjacent to the metal disperser, U.S. Pat. No. 4,771,783 (Roberts) shows a biomedical electrode having an electrically conductive metal film connected through the edge of the electrode to a lead wire, U.S. Pat. No. 4,911,657 (Berlin) shows an EKG electrode having a metal layer and gel matrix with a plug insertable through an insulating sheet to the metal layer, U.S. Pat. No. 4,895,169 (Heath) shows a stimulating electrode having a metal conductive plate, a porous foam disc to receive saline gel, and a holding ring at the opposite side from the foam base, and U.S. Pat. No. 4,893,626 (Henley et al.) shows an electrode having a natural rubber insulating layer next to an adhesive tape backing and an aqueous gel layer that is conductive.

U.S. Pat. No. 4,635,642 (Cartmell et al.) shows a disposable electrode having spaced foam sheets, hydrogel between the sheets, and a plug-in connector insertable through a hole in the top of one sheet, U.S. Pat. No. 4,243,051 (Wittemann) shows a disposable electrode with a mesh disperser that includes a metal and a fabric backing with the disperser connected to a wire lead that is positioned across the disperser, and U.S. Pat. No. 4,237,886 (Sakurada et al.) shows an electrode having a substrate that includes a textile with conductive fibers and a conductive adhesive layer that includes carbon fibers.

U.S. Pat. No. 4,798,208 (Faasse, Jr.) shows a diagnostic electrode with a tab extending from one edge thereof that is engagable by an alligator-type clip, and U.S. Pat. No. 4,657,023 (Kuhn) shows an electrode for use with ECG measuring apparatus having a metallic layer with an upwardly extending tab engagable with an alligator-type clip.

The use of electrical apparatus and methods for enhancing healing of a soft tissue wound is shown in U.S. Pat. No. 4,846,181 (Miller) and apparatus for enhancing healing of a soft tissue wound is shown in U.S. Pat. No. 4,895,154 (Bartelt et al.) both which are owned by the assignee of this invention. U.S. Pat. No. 4,738,250 (Fulkerson et al.), U.S. Pat. No. 4,919,138 (Nordenstroom), U.S. Pat. No. 4,922,906 (Takeuchi et al.) and U.S. Pat. No. 4,895,153 (Takeuchi et al.) also show apparatus for applying electronic signals to a wound area to facilitate healing.

As can be appreciated from the foregoing, while electrodes, associated connectors and/or methods of utilization have heretofore been suggested for various purposes including enhancing wound treatment, improvements can still be utilized to good advantage.

SUMMARY OF THE INVENTION

This invention provides an improved electrode, combination and a method for utilization. The electrode of this invention will tolerate sterilization, is not subject to ion migration (which can occur where the electrode includes metal), toxicity (which can occur when the electrode includes toxic chemicals), shedding of particles and/or corrosion, is biocompatible and rated for blood contact, is flexible to allow contouring to the wound, provides uniform current density under the disperser sheet of the electrode, provides the proper moist environment to promote healing at the wound site, is non-adhering to the wound site, and is formed of sufficiently low cost materials with low cost assembly to allow practical use of the electrode as a disposable electrode intended for short term application.

The releasable connector utilizable in combination with the electrode allows delivery of an electrical signal to the electrode and, in addition, the connector and electrode are configured to enable the connector to be used as a tool, as a method of utilization, to facilitate disposal of the electrode.

It is therefore an object of this invention to provide an improved electrode.

It is still another object of this invention to provide an improved electrode that is useful for enhancing wound treatment.

It is still another object of this invention to provide an improved electrode that utilizes a nonmetallic disperser that is formed at least in part by carbon.

It is still another object of this invention to provide an improved electrode having an improved connector utilizable in combination therewith.

It is still another object of this invention to provide an improved electrode and releasable connector combination to facilitate disposal of a used electrode.

It is still another object of this invention to provide an improved system for treatment of a soft tissue wound.

It is still another object of this invention to provide an improved method for utilization of an electrode and connector combination.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 illustrates an overall system useful for enhancing wound treatment using this invention;

FIG. 2 is a perspective view of the electrode of this invention;

FIG. 3 is a cut-away top view of the electrode shown in FIG. 2;

FIG. 4 is a cross sectional side view taken through lines 4—4 of the electrode shown in FIG. 3;

FIG. 6 is a perspective view of the releasable connector utilized in this invention.

DESCRIPTION OF THE INVENTION

Figure 5:
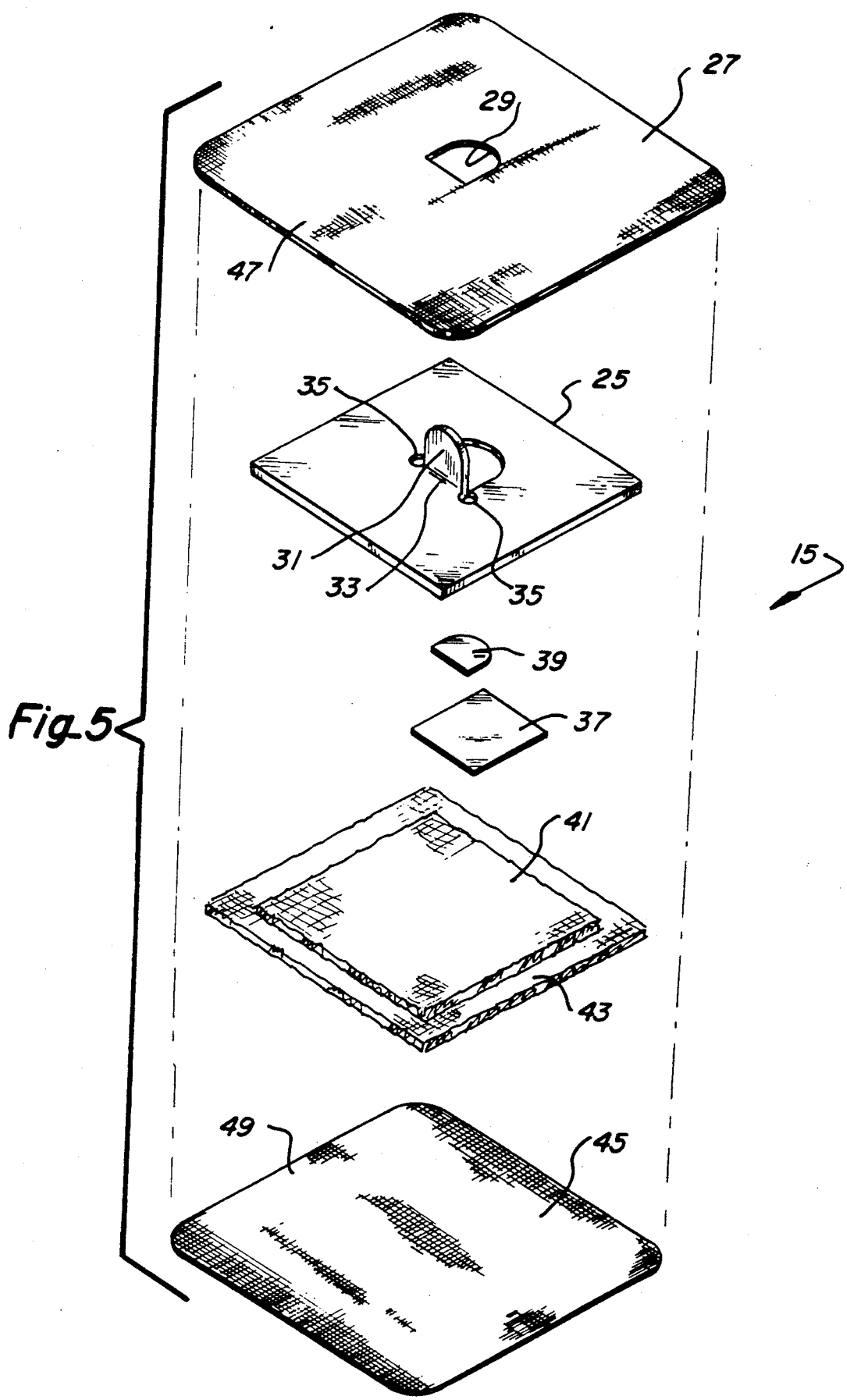
FIG. 5 is an exploded perspective view of the electrode shown in FIGS. 1 through 4.

As indicated in FIG. 1, signal generator 9 provides an electrical output signal, and this electrical output signal is coupled through cable 11, connector 13, and active electrode 15 to soft tissue wound site 17 of patient 19. As is conventional, a return electrode 21 engages a separate area of the patient spaced from the wound site, and a return path to generator 9 is provided through cable 23.

Wound healing signal generator 9 provides an electrical output signal that is suitable for enhancing wound healing. Generator 9 may be a known type, and may be, for example, a generator as described in U.S. Pat. No. 4,895,154 (Bartelt et al.).

For use as a wound treatment electrode, connector 13 transfers current into the electrode so that the current density remains substantially uniform. Wound treatment is intended to enhance at least wound healing, but with a suitable electrical signal supplied by generator 9, could also enhance edema reduction and/or provide pain suppression. In addition, connector 13 is configured to retard corrosion due to such factors as seepage of fluid from electrode 15.

Active electrode 15 includes a disperser 25 that is preferably non-metallic and is formed at least in part by carbon. Disperser 25 is now preferably a sheet that is configured to be highly conductive (less than 4 ohms/-square being preferred) so that the current density under the electrode is essentially flat over substantially the entire surface of the sheet, provides a soft, flexible, moist, and conforming engagement with the wound to be treated, is biocompatible and rated for blood contact (even with DC applied current) with no ion migration, is sterilizable (including gamma ray sterilization without causing chemical breakdown, unacceptable color change or loss of suppleness or strength), does not undergo electrolysis so as to deposit metal ions or other toxic materials into the wound, and is relatively easy and inexpensive to manufacture.

The foregoing is achieved with respect to electrode 15 by utilizing a multi-layer arrangement as shown in FIGS. 2 through 5. As shown, an outer, or cover, layer 27 (preferably an electrically non-conductive, apertured polyester, non-woven, fabric composition laminated to a white polyethylene thin film that is waterproof, and having an adhesive on one side) has an aperture 29 formed, or cut, in the interior thereof (and preferably centrally positioned within the cover layer). The inner (adhesive) side of cover layer, or sheet, 27 engages one side of electrically conductive, disperser layer 25.

Disperser 25 is now preferably a flexible, extruded carbon-containing silicone rubber sheet (preferably 50% carbon by weight) having no metal oxides or fillers, although other dispersers might be utilized, including dispersers formed of woven graphite cloth. In addition, carbon fibers might also be utilized with the fibers woven of themselves and/or included in a woven or non-woven electrically non-conductive carrier material, with such fibers being pitch or pan (polyacrylic nitrile) carbon fibers chosen for their low electrical resistivity, nearly pure (99%+) carbon composition, biocompatibility, low cost, and ease of manufacture.

Disperser 25 has fold-out connector tab 31 integrally formed as a part of the disperser, and tab 31 extends outwardly from a junction 33 formed with the remainder of disperser sheet 25 at the interior (preferably central) portion of the disperser layer (to improve the uniformity of current distribution). Tab 31 is extendable through aperture 29 in cover layer 27, with the aperture being preferably of substantially the same dimensions as is the tab (to assure that the tab and aperture have the same dimensions, they may be cut at the same time when the electrode is made). If carbon fibers can be utilized, a lead wire extending through aperture 29 in cover sheet 25 could be an extended carbon fiber.

Disperser 25 is thin (preferably having a thickness of about 0.045 inches for a carbon-containing silicone rubber sheet) and is flexible so that the disperser can be closely contoured to the wound. Tab 31 preferably has holes, or apertures, 35 formed in the disperser tangent to the tops of the U-shaped tab so that the cut ends of the tabs are a radius contour rather than a sharp point where force can concentrate (this has been found to reduce susceptibility of the tab to being severed from the remainder of the disperser layer and thus provides tab protection).

In addition, a reinforcing, or support, strip 37 (preferably a layer of polyethylene tape although medical grade adhesive tape could also be used) covers the entire U-shaped tab and the area immediately adjacent thereto at the side of disperser layer 25 opposite to that in engagement with cover layer 27, and a film, or ribbon, 39 (preferably a polyester film) of the same size as tab 31 is positioned on tape strip 37 at the same side as is tab 31. Tape strip 37 absorbs force to also protect the tab against severance from the remainder of the disperser, and the tape strip and polyester ribbon provide a fluid seal at aperture 29 to prevent seepage of fluid from the electrode at the cover side (this provides protection to the releasable connector (also positioned at the cover side of the electrode) from corrosion where saline solution, for example, is used in the electrode).

Support strip 37 preferably covers only a small area relative to the size of the disperser since strip 37 is non-conductive, and ribbon segment 39 is preferably of the same size as the tab and is positioned in good alignment therewith. The ribbon segment prevents sticking of the tab to the tape strip.

Sponge-like material is now preferably used to retain saline solution to moisturize the wound to be treated. This may be implemented by using one layer or, more preferably, by using a pair of absorbant sponge-like layers, or sheets, 41 and 43 (preferably gauze sponges, or pads, made from rayon polyester blend, although urethane foam might also be utilized) to be filled, or saturated, with saline solution, with the layers positioned side-by-side in the electrode to provide a fluid retainer conductive medium (electrically conductive hydrogel may also be utilized in some cases in lieu of a gauze sponge). As shown, one side of layer 41 is in engagement with the side of disperser 25 opposite to the side in engagement with cover sheet 27.

A layer, or sheet, of wound contacting material (preferably contact fabric) 45 has one side in engagement with one side of sponge layer 43. The other side of contact fabric 45 is directly engagable with the soft tissue wound to be treated, and contact fabric 45 therefore needs to be non-adherent to such a wound (contact fabric 45 is preferably a wound dressing material such as described in U.S. Pat. No. 4,638,796). Where a sheet of electrically conductive hydrogel is utilized, this sheet, if substantially non-adhering to the wound, might be used, at least in some cases, as the wound contacting sheet and thereby eliminate the need for the gauze layer or layers.

Fabric cover layer 27 and wound contact layer 45 have substantially the same dimensions, and, as illustrated best in FIGS. 4 and 5, are larger than disperser layer 25 and sponge layers 41 and 43. As shown, the peripheries 47 and 49 of layers 27 and 45, respectively, are sealed together (by adhesive or heat sealing, for example) to provide an envelope, or bag, having the dispersive layer and the sponge layers (if utilized) enclosed therein. Outer cover sheet 27 and wound contact sheet 45 are preferably porous to the extent that the outer layer has the ability to pass water vapor into the air while retaining the fluid (saline solution) within the envelope, and the wound contact layer has the ability to pass fluid (saline solution) to the extent necessary to moisturize the wound.

While not specifically shown, a removable release paper backing may be provided at the side of cover layer 27 opposite to the side engaging disperser layer 31, and the entire assembled electrode may be stored, until use, in a container, such as a sealed paper container.

The dimensions of the electrode may be varied, as needed, so long as the disperser and the fluid retainer/conductive medium are sufficiently small to be inserted into the envelope formed by the cover sheet and the wound contact sheet, with the portion of the disperser extending from the electrodes being configured to readily permit gripping by the releasable connector.

By way of example, a cover sheet and a wound contact sheet of about 4.2 inches square, a disperser sheet of about 3 inches square, fluid retainers of about 3.2 and 3.5 inches square, a tab of about 0.48 inches in length and 0.56 inches width, a protector tab strip of about 1 inch in length and 0.75 inches in width, and a total thickness of the electrode of between about 0.25 inches to 0.50 inches, has proved to be an effective combination, utilizable in conjunction with a releasable clip of about 1 inch in length.

Releasable connector 13, as shown in FIG. 6, is preferably an alligator-type clip that readily allows clamping of the connector onto tab 31. As shown, connector 13 includes two opposing segments, or arms, 51 and 53, each of which includes a jaw portion 55 having a small (preferably circular) metal-toothed gripping portion 57 (the metal teeth are preferably gold-plated to retard corrosion), and a handle portion 59. The segments are mounted for rotation with respect to one another about pin 61 so that jaw portions 55 oppose one another and are movable to bring the gripping portions 57 into and out of contact with one another as is common to an alligator-type clip. Spring 63 is utilized at handle portions 59 to bias the jaw portions toward one another.

Connector 13 includes a housing preferably made of plastic material, except for the gripping portions and spring. Cable 11 provides an electrical connection to connector 13 from generator 9. Cable 11 preferably includes a pair of leads 65 and 67, with lead 65 providing current to jaw gripping portion 57 of connector segment 51, and with lead 67 providing current to jaw gripping portion 57 of connector segment 59, as indicated in FIG. 6.

Leads 65 and 67 are preferably kept completely insulated, insofar as is practical, and are connected to the toothed areas inside the plastic housing at the jaw portions to better provide insulation to the connecting wires. In this manner, the connector is minimally exposed to the danger of corrosion due to fluid escaping from the electrode and contact impedance is minimized. In addition, even though the spring is exposed to fluid from the electrode, the spring is not subject to electrically accelerated corrosion since the spring receives no treatment current (the jaw gripping portions are directly connected to leads 65 and 67).

Connector 13 not only provides an effective and reliable connection to the connector tab of the electrode, but, in addition, provides a tool to facilitate handling of the electrode, and particularly for use in disposing of a used electrode.

The electrode, after assembly (and normally with no saline solution in the retainer pads if such pads are utilized), is placed in a sealed package, gamma ray sterilized, and then stored until use. When needed, the package containing the electrode is opened, saline solution is added to the retainer pads (if such pads have been utilized), and the backing on the cover sheet is removed (if such a backing has been used). Connector 13 is clamped onto the electrode tab 31, making sure that the teeth of the jaws are firmly in engagement with the electrically conductive tab, the electrode is placed on the wound and retained thereon by use of paper tape, or the like, placed over the cover sheet and extending to skin contact beyond the wound to be treated. After placement of the electrode on the wound, treatment is commenced.

After use of the electrode in treating a wound by application of an electrical signal through the connector and electrode to the wound, the connector may then be used as a tool to remove the used electrode from wound contact without requiring physical contact with the electrode. The electrode is intended for one-time temporary use (the connector, on the other hand, is intended for continued use with other electrodes), and the used electrode can be directly delivered by the connector to a disposal unit after use. To facilitate use of the releasable connector as a tool to dispose of a used electrode, the cable 11 may be disconnected from generator 9 (cables 11 and 23 are normally connected with generator 9 through the use of pin-type plugs or the like).

At the disposal unit, the handle portions of the connector are moved toward one another to overcome the spring bias and move the connector jaws away from one another to release the electrode and allow deposit the electrode into the disposal unit. Convenience in handling and disposing of the used electrode is therefore enhanced, with isolation of the electrode being maintained throughout disposal to thereby aid in protection of the person responsible for disposing of the electrode, as well as preventing the spread of wound bacteria and the like. In accordance with accepted treatment practice, and particularly where treating open wounds, it is to be realized that a person responsible for treatment and/or electrode disposal would be expected to take normal precautions, including, but not necessarily limited to, wearing protective gloves while contacting and/or handling the electrode and/or the connector, and, particularly, in contacting and/or handling the electrode and/or connector after use of the electrode.

While a preferred embodiment is set forth herein, it is to be realized that elements of the embodiment as shown may be modified (including, but not limited to, modifications as set forth herein) without departing from the intended scope of this invention.

As can be appreciated from the foregoing, this invention provides for improved wound treatment, including providing an improved electrode, combination and method for utilization.

What is claimed is:

1. An electrode assembly for use in treatment of a soft tissue wound, said electrode assembly comprising:
   an electrically non-conductive sheet having an aperture therein;
   an electrically conductive, non-metallic disperser sheet formed at least in part by carbon, said conductive sheet having first and second sides with said first side facing said non-conductive sheet, and said conductive sheet having a portion of said sheet extending through said aperture in said non-conductive sheet to enable connection of said conductive sheet with a signal source capable of providing an electrical signal suitable for application to said soft tissue wound to promote treatment thereof, said portion of conductive sheet extending through said aperture in said non-conductive sheet being one of an electrically conductive tab and an electrically conductive lead integral with the remainder of said conductive sheet;
   a substantially non-adhering wound contact sheet having a first side facing said second side of said conductive sheet, and a second side for engaging said soft tissue wound; and sealing means positioned between said wound contact sheet and said aperture in said non-conductive sheet.

2. The electrode assembly of claim 1 wherein said electrically non-conductive sheet is a non-woven porous fabric film composition.

3. The electrode assembly of claim 1 wherein said conductive sheet is a thin, readily flexible sheet of carbon-containing silicone rubber.

4. The electrode assembly of claim 3 wherein said carbon-containing silicone rubber is extruded and substantially free of oxides and fillers.

5. The electrode assembly of claim 1 wherein said conductive sheet includes carbon fiber.

6. The electrode assembly of claim 5 wherein said carbon fiber is woven to form a conductive mesh disperser.

7. The electrode assembly of claim 6 wherein said carbon fiber is woven with a non-conductive material to form a conductive mesh disperser.

8. The electrode assembly of claim 7 wherein said non-conductive material is graphite cloth.

9. The electrode assembly of claim 1 wherein said portion is a tab, wherein said aperture is substantially equal in size to said tab, and wherein said sealing means includes an electrically non-conductive strip slightly larger than said aperture with said non-conductive strip being positioned at said second side of said conductive sheet.

10. The electrode assembly of claim 1 wherein said electrode assembly includes fluid-state electrically conductive means for wound moisturizing, said fluid-state electrically conductive means being between said second side of said conductive disperser sheet and said first side of said wound contact sheet.

11. The electrode assembly of claim 10 wherein said electrode assembly includes fluid retaining means, and wherein said fluid-state conductive means is a saline solution in said fluid retaining means.

12. The electrode assembly of claim 11 wherein said fluid retaining means includes at least one layer of sponge-like rayon/polyester blend material.

13. The electrode assembly of claim 1 wherein said wound contact sheet is a contact fabric that is substantially non-adhering to a wound.

14. The electrode assembly of claim 1 wherein said substantially non-adhering wound contact sheet is a sheet of electrically conductive hydrogel.

15. An electrode assembly for use in treatment of a soft tissue wound, said electrode assembly comprising:
an electrically non-conductive sheet having an aperture therein;
an electrically conductive disperser sheet having first and second sides with said first side facing said non-conductive sheet, and said conductive sheet having an electrically conductive tab extending through said aperture in said non-conductive sheet to enable connection of said conductive sheet with a signal source capable of providing an electrical signal suitable for application to said soft tissue wound to promote treatment thereof;
fluid retaining means at said second side of said conductive sheet for receiving and retaining an electrically conductive fluid;
sealing means positioned adjacent to said tab and between said fluid retaining means and said aperture in said non-conductive sheet for substantially sealing said electrode assembly at said aperture with said tab extending through said aperture; and
a substantially non-adhering wound contact sheet having a first side facing said second side of said conductive sheet with said fluid retaining means being between said wound contact sheet and said conductive sheet, and a second side for engaging said soft tissue wound.

16. An electrode assembly for use in treatment of a soft tissue wound, said electrode assembly comprising:
an electrically non-conductive sheet having an aperture therein;
electrically conductive, non-metallic disperser means for providing an electrical signal to said soft tissue wound, said conductive means being formed at least in part by carbon, said conductive means having first and second sides with said first side facing said non-conductive sheet, and said conductive means having a portion extendable through said aperture in said non-conductive sheet to enable connection of said conductive means with a signal source capable of providing an electrical signal suitable for application to said soft tissue wound to promote treatment thereof; and
a substantially non-adhering wound contact sheet of electrically conductive hydrogel having a first side facing said second side of said conductive means, and a second side for engaging said soft tissue wound.

17. An electrode assembly for use in enhancing treatment of a wound, said electrode assembly comprising:
an electrically non-conductive sheet having a central portion and surrounding edge portions with said central portion having an aperture therein;
an electrically conductive sheet one side of which is contiguous to said non-conductive sheet, said conductive sheet having a central portion and surrounding edge portions with said central portion having a connector tab portion extending from said central portion of said conductive sheet and extending through said aperture in said non-conductive sheet to enable connection of said conductive sheet with a signal source capable of providing a treatment signal to said conductive sheet;
fluid retaining means at the other side of said conductive sheet for receiving and retaining an electrically conductive fluid;
sealing means larger than said aperture in said non-conductive sheet and smaller than said conductive sheet, said sealing means being between said conductive sheet and said fluid retaining means and adjacent to said connector tab portion to provide a seal for said aperture in said non-conductive sheet; and
a wound contact sheet at the other side of said conductive sheet and having said fluid retaining means and said sealing means between said wound contact sheet and said conductive sheet, said wound contact sheet being substantially non-adhering for contact with a wound to be treated by application of an electrical signal applied to said wound through said electrode assembly.

18. The electrode assembly of claim 19 wherein said electrode assembly includes tab protector means for protecting said connector tab portion against severance from the remainder of said conductive sheet, said tab protector means including at least one of a material strip engaging said conductive sheet adjacent to said connector tab portion and apertures adjacent to the junction of said connector tab portion and the remainder of said conductive sheet.

19. A disposable electrode assembly for use in enhancing treatment of a soft tissue wound, said electrode assembly comprising:
an electrically non-conductive cover sheet having outer and inner sides each of which has an interior portion and a periphery surrounding said interior portion;

an electrically conductive, non-metallic disperser sheet formed from carbon-containing silicone rubber, said disperser sheet having first and second sides with said first side engaging said interior portion of said inner side of said cover sheet, and said disperser sheet being adapted to be connected with an electrical signal source capable of providing an electrical signal to said disperser sheet;

a sealing strip at said second side of said disperser sheet, said sealing strip being much smaller than said disperser sheet;

fluid retaining means having first and second sides with said first side engaging said second side of said disperser sheet and said sealing strip, and said fluid retaining means being adapted to receive and retain a saline solution; and a substantially non-adhering wound contact sheet having inner and outer sides with said inner side having an interior portion and a periphery surrounding said interior portion, and with said outer side being engagable with a soft tissue wound to be treated by application of an electrical signal thereto, said interior portion of said inner side engaging said fluid retaining means, and said periphery of said inner side of said wound contact sheet engaging said periphery of said inner side of said cover sheet to form a closed envelope having said disperser sheet and said fluid retaining means therein.

20. The electrode assembly of claim 19 wherein said disperser sheet includes a tab extending through said cover sheet to adapt said disperser sheet to be connected with an electrical signal source, said tab being configured to have a releasable connector readily clamped thereto.

* * * * *